United States Patent [19]

Kato et al.

[11] 4,444,872
[45] Apr. 24, 1984

[54] METHOD AND MATERIAL FOR THE FORMATION OF SILVER HALIDE COLOR PHOTOGRAPHIC IMAGE

[75] Inventors: Katsunori Kato, Hachioji; Ryosuke Sato, Hino, both of Japan

[73] Assignee: Konishiroku Photo Industry Co., Ltd., Tokyo, Japan

[21] Appl. No.: 406,945

[22] Filed: Aug. 10, 1982

[30] Foreign Application Priority Data

Aug. 20, 1981 [JP] Japan ................ 56-131312

[51] Int. Cl.$^3$ .................. G03C 7/16; G03C 7/26
[52] U.S. Cl. .................... 430/384; 430/385; 430/552; 430/553; 430/558
[58] Field of Search ........... 430/384, 385, 552, 553, 430/558

[56] References Cited

U.S. PATENT DOCUMENTS

| | | | |
|---|---|---|---|
| 3,446,622 | 5/1969 | Magagnoli et al. | 430/552 |
| 3,681,076 | 8/1972 | Skoog | 430/552 |
| 3,758,308 | 9/1973 | Beavers et al. | 430/553 |
| 3,772,002 | 11/1973 | Ramello | 430/553 |
| 3,880,661 | 4/1975 | Lau et al. | 430/553 |
| 4,333,999 | 6/1982 | Lau | 430/385 |

*Primary Examiner*—J. Travis Brown
*Attorney, Agent, or Firm*—Finnegan, Henderson, Farabow, Garrett & Dunner

[57] ABSTRACT

A method for forming a silver halide color photographic image comprising forming a dye image in the presence of a phenol cyan coupler. The phenol cyan coupler has the following formula:

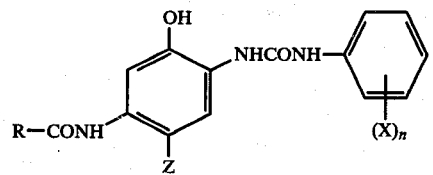

wherein R is an alkyl, an aryl or a heterocyclic group; X is selected from the group consisting of an alkyl, acyloxy, acylamino, succinimide, and sulfoneamide moiety; Z is a hydrogen atom or a group capable of eliminating itself from the coupler during the coupling reaction with the oxidized product of a color developing agent; and n is an integer from 1 to 3, and when n is 2 or 3, X may be the same or different.

6 Claims, No Drawings

METHOD AND MATERIAL FOR THE FORMATION OF SILVER HALIDE COLOR PHOTOGRAPHIC IMAGE

The present invention relates to a silver halide color photographic light-sensitive material containing a novel cyan dye image forming coupler. A color photographic image is normally formed by the oxidation coupling reactions effected inside a silver halide emulsion between the oxidized product of a color developing agent produced during the reduction of the exposed silver halide particles by an aromatic primary amine color developing agent and couplers to form yellow, magenta and cyan dyes.

Typical couplers for use in the formation of cyan dyes are phenols and naphthols. Those fundamental requirements which have conventionally been considered to be essential for the photographic characteristics, particularly, of phenols and couplers are that the dye formed from the coupler is to have a satisfactory spectral absorption characteristics; i.e., to have a sharp-cut filtering effect with no absorption in the green region of the spectra; the formed dye is to have a sufficient durability against light, heat, moisture, and the like; the coupler is to be excellent in the color developability; i.e., to have a sufficiently color-developable sensitivity and color developed density; and no loss of the dye formation is to occur even in the running processing during which the bleaching bath of bleach-fixing bath composed principally of the ferric salt of EDTA becomes exhausted.

From the untipollution point of view, benzyl alcohol to be added to the color developing bath is desirable to be removed from the bath, but the addition of the alcohol to the color developing bath is essential for attaining a sufficient color developability; this has been in serious question. The deterioration of the color developability due to the removal of benzyl alcohol is particularly noticeable in the case of cyan couplers. For this reason, the development of a benzyl alcohol-free high color developability-having phenol cyan coupler has been of urgent necessity.

Many attempts have hitherto been made to satisfy the above-described requirements, but so far as we know, there have been found no cyan couplers that can satisfy all the characteristics required as mentioned in above.

For example, the 6-8 α-(2,4-di-t-amyl phenoxy)-butaneamidel]-2,4-di-chloro-3-methyl phenol as described in U.S. Pat. No. 2,801,171 is excellent in the light resistance, but is disadvantageous because of the unsatisfactory heat resistance, and in addition, because of the loss of the resulting dye in the exhausted bleach-fixing solution. Further, the color developability depends largely upon benzyl alcohol, so that it is difficult to remove benzyl alcohol from the color developing solution. The 2-heptafluorobutaneamide-5-[α-(2,4-di-t-amylphenoxy)hexaneamide]phenol as described in U.S. Pat. No. 2,895,826 is excellent in that there is little loss of the dye in the exhausted bleach-fixing bath as well as in the heat resistance, but is disadvantageous in the color developability as well as the light resistance. The coupler as described in Japanese Patent Publicatipon Open to Public Inspection (hereinafter referred to as Japanese Patent O.P.I. Publication) No. 109630/1978 also poses a problem to the light resistance as well as to the removal of benzyl alcohol. Further, those phenol cyan couplers as described in U.S. Pat. No. 3,839,044, Japanese Patent O.P.I. Publication No. 37425/1972, Japanese Patent Examined Publication No. 36894/1973, Japanese Patent O.P.I. Publication Nos. 10135/1975, 117422/1975, 108841/1975, 120334/1975, and the like also are unsatisfactory in the removal of benzyl alcohol. Those phenol couplers having a ureide group in the second position thereof are described in British Pat. No. 1,011,940 and U.S. Pat. Nos. 3,446,622, 3,996,253, 3,758,308 and 3,880,661, but those cyan dyes formed from these couplers have broader spectral absorptions whose absorption maximums are located in relatively shorter wavelengths in the red region of the spectra, so that they are not acceptable for the color reproduction. The phenol coupler having a ureide group in the second position thereof as described in Japanese Patent O.P.I. Publication No. 65134/1981 is one that is fairly improved in the absorption of the green region in the spectra, but is still not sufficient in respect of other characteristics.

As a result of having been devoting ourselves to studies on how to overcome the difficulty in the removal of benzyl alcohol that has not been attained by the prior art, we have found that a coupler having the formula given below can fully satisfy all the requirements essential for such phenol cyan couplers as has been mentioned; that is, the object of the present invention has been accomplished by the formation of a cyan dye image in the presence of a phenol cyan coupler having in the second position thereof a phenyl ureide group substituted by a group selected from the class consisting of an alkyl group, an aryl group, a heterocyclic group, hydroxy group, an alkoxy group, an aryloxy group, an acyloxy group, an alkyl-thio group, an acylamino group and a sulfoneamide group; having in the fourth position thereof a hydrogen atom or a group capable of eliminating itself during the coupling reaction between the oxidized product of the color developing agent and the coupler; and having in the fifth position thereof an acylamino group.

The preferable cyan coupler in the present invention has the formula:

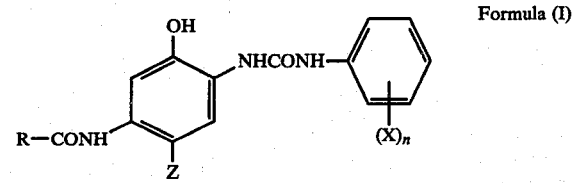

Formula (I)

wherein R is a substituted or unsubstituted alkyl having from 1 to 20 carbon atoms (preferably a phenoxyalkyl), a substituted or unsubstituted aryl group (preferably a phenyl group) or a heterocyclic group (e.g., a nitrogen-containing heterocyclic group such as piperidine or pyrrolidone); X is a group selected from the group consisting of a substituted or unsubstituted alkyl group having from 1 to 8 carbon atoms, substituted or unsubstituted phenyl, a heterocyclic group preferably a nitrogen-containing heterocyclic group such as piperidine, or pyrrolidine), hydroxy group, a substituted or unsubstituted alkoxy group having from 1 to 8 carbon atoms, phenoxy group, a substituted or unsubstituted alkoxycarbonyloxy group having from 1 to 20 carbon atoms, benzoyloxy group, a substituted or unsubstituted alkylthio group having from 1 to 20 carbon atoms, a substituted or unsubstituted alkyl carbamide group having from 1 to 20 carbon atoms, benzoylamide group, a substituted or unsubstituted alkyl sulfoneamide group (allowed to be cyclic) having from 1 to 20 carbon atoms, and a benzene sulfoneamide group; those groups useful for substituting the phenyl or aryl group of the phenoxyalkyl represented by the R include, e.g., a halogen, a substituted or unsubstituted alkyl, hydroxy, alkoxy, acyloxy, alkyl-thio, aryl-thio, alkyl-sulfonyl, aryl-sulfonyl, alkoxycarbonyl, aryloxycarbonyl, acyl, alkyl-sulfonyl, aryl-sulfonyl, acylamino, carbamoyl, sulfoneamide sulfamoyl, nitro, cyano groups and the like from which an arbitrary one may be selected; Z represents hydrogen or such a group capable of eliminating itself during the coupling reaction of the coupler with the oxidized product of a color developing agent as, e.g, a halogen (such as chlorine, bromine, fluorine), an aryloxy group in which oxygen or nitrogen is directly attached to the coupling position thereof, carbamoyloxy, carbamoylmethoxy, acyloxy, sulfoneamide, succinic acid imide group, or the like, further examples of the Z being described in U.S. Pat. No. 3,471,563, Japanese Patent O.P.I. Publication No. 37425/1972, Japanese Patent Examined Publication No. 36894/1973, Japanese Patent O.P.I. Publication Nos. 10135/1975, 117422/1975, 130441/1975, 108841/1976, 120334/1975, 18315/1977, 52423/1978, 105226/1978, and the like; and n is an integer of from 1 to 3, provided when n is not less than 2, each X is allowed to be either the same or different.

Those cyan couplers as defined in the claims of the present invention are exemplified below, but are not limited to the following examples:

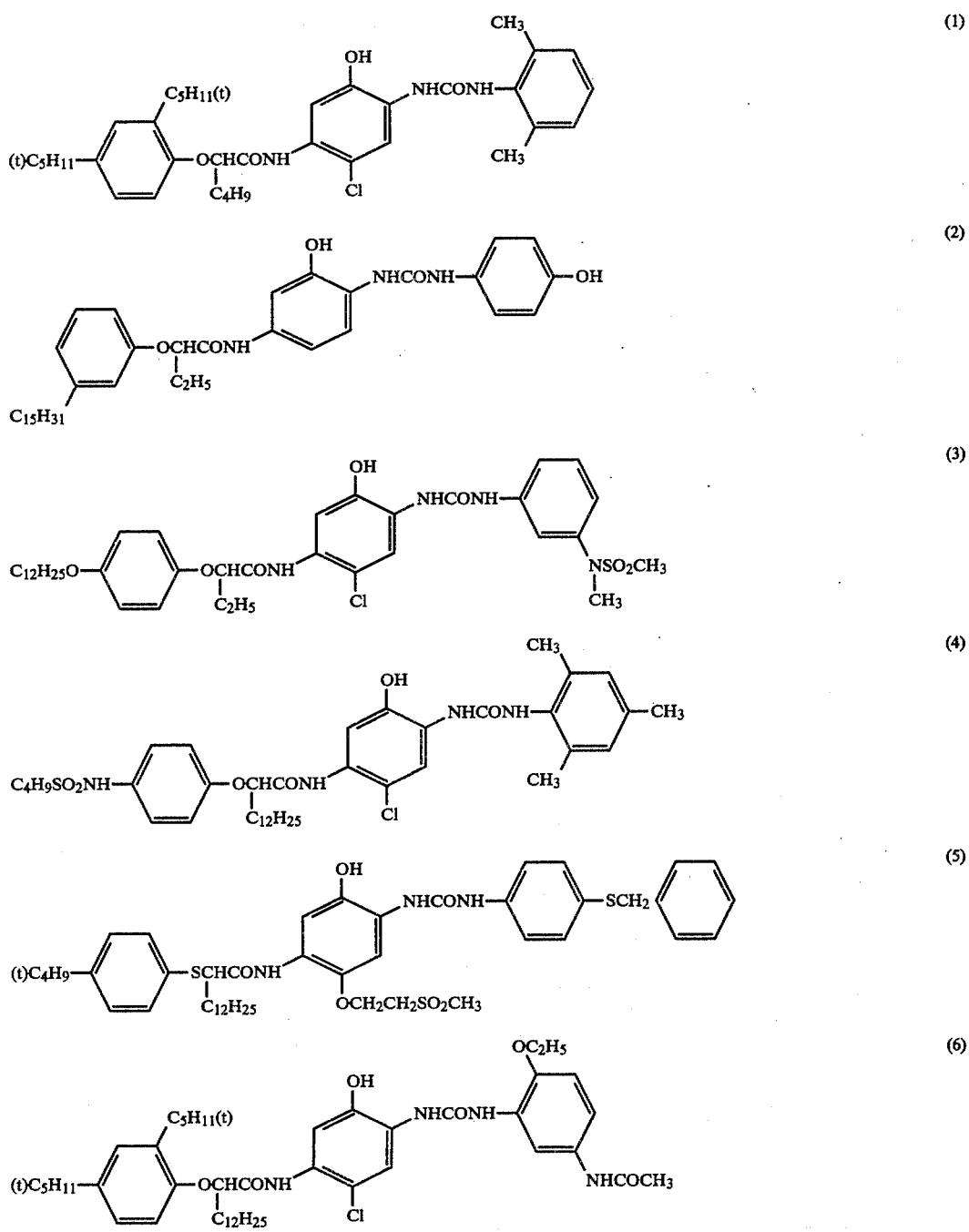

-continued
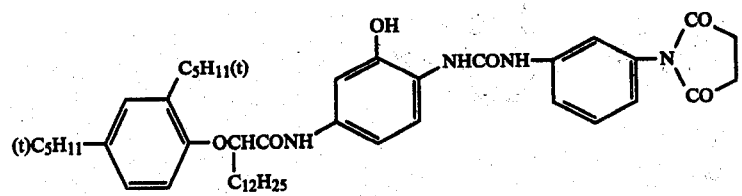
(7)
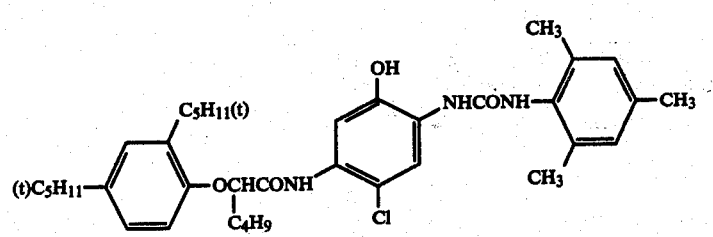
(8)
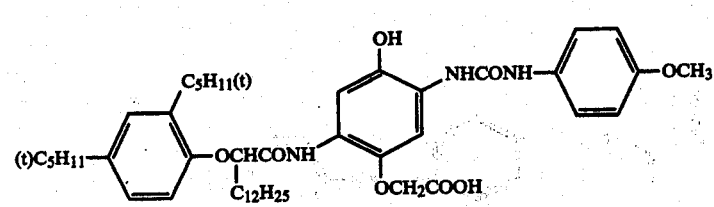
(9)
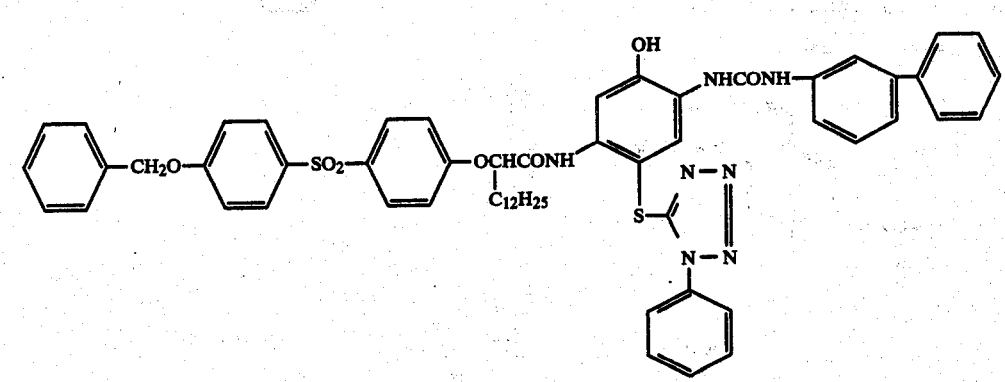
(10)
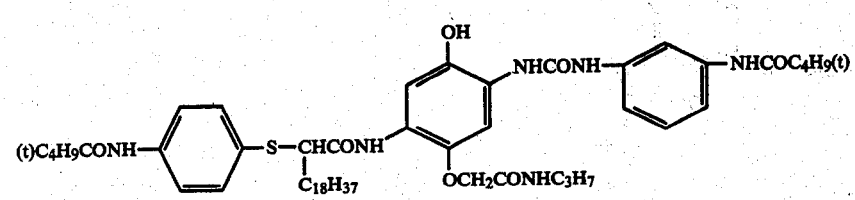
(11)
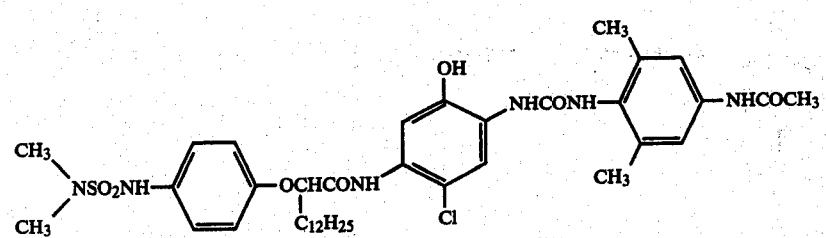
(12)
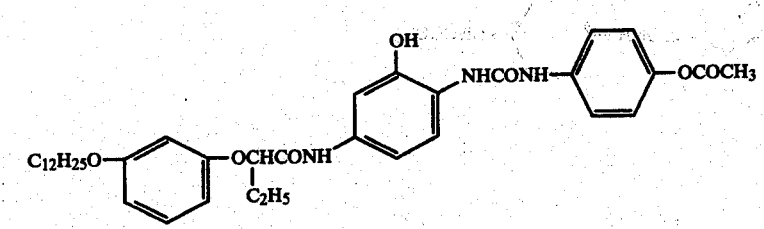
(13)

-continued
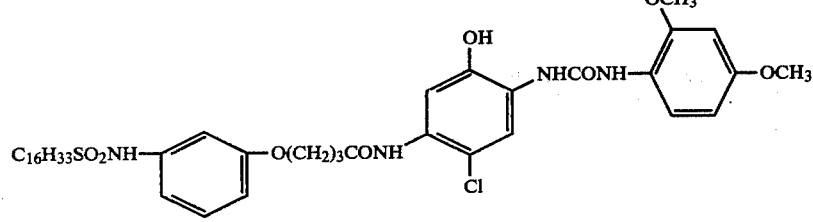
(14)
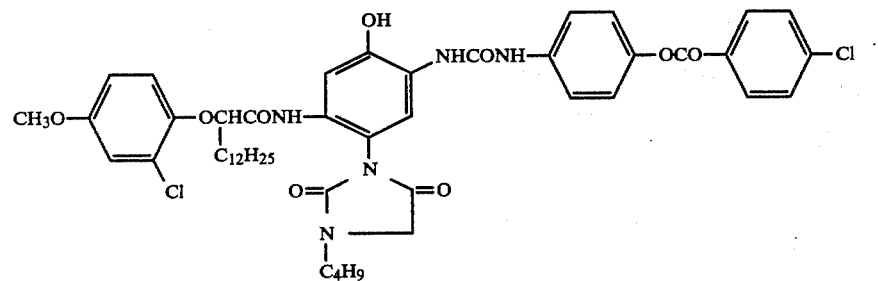
(15)
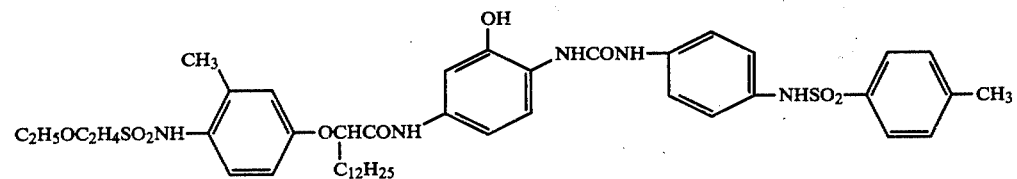
(16)
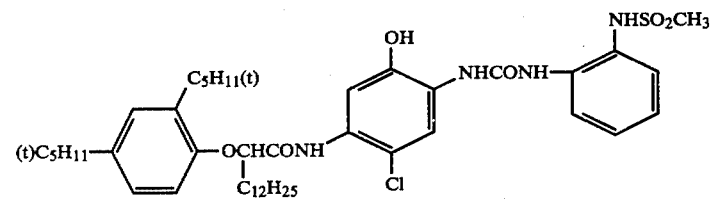
(17)
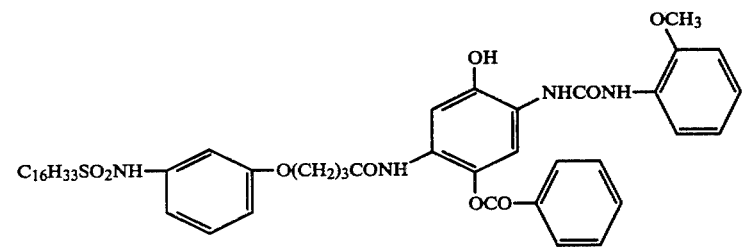
(18)
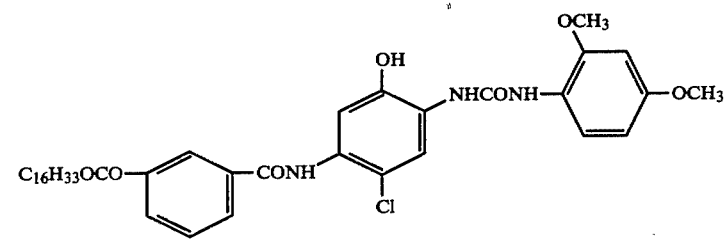
(19)
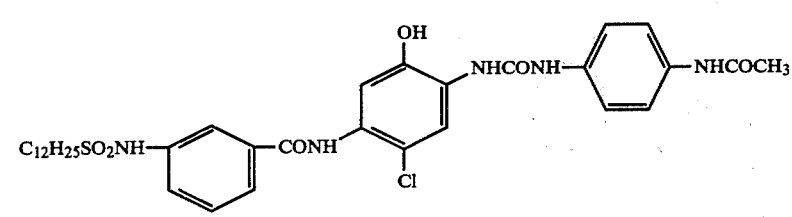
(20)

The following are typical synthesizing steps and synthesis examples of the couplers of the present invention:

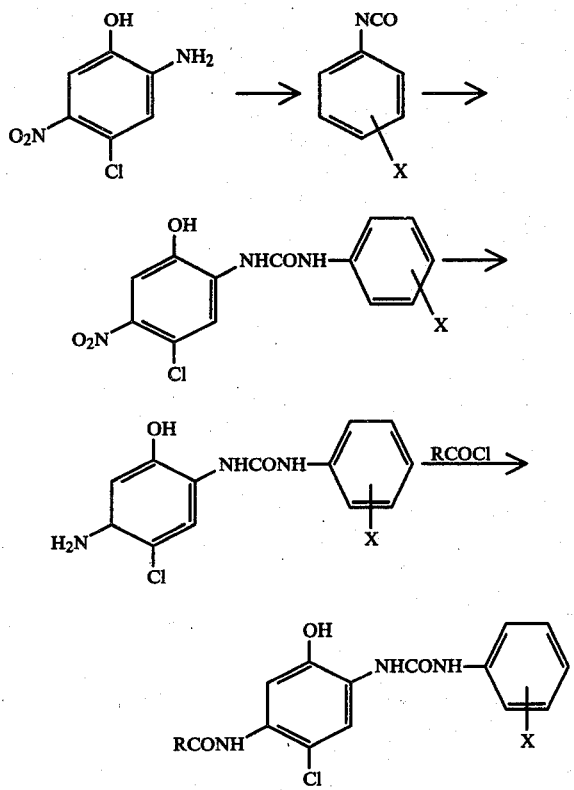

SYNTHESIS EXAMPLE 1

(Synthesis of Exemplified Coupler 14)

Synthesis of 4-chloro-5-[3-{3(hexadecyl-sulfoneamide) phenoxy}butaneamide]-2-(2,4-dimethoxyphenyl ureide)phenol.

18.9 g of 2-amino-4-chloro-5-nitrophenol were dispersed into 200 ml of toluene, and to the mixture were added with stirring at room temperature 100 ml of a toluene solution containing 18.0 g of 2,4-dimethoxyphenylisocyanate. The resulting reaction mixture was boiled with refluxing for 1 hour. After cooling to room temperature, the deposited crystals were collected by filtration and washed with methanol, whereby 31 g of yellow crystals were obtained.

18 g of 4-chloro-2-(2,4-dimethoxy-pjenyl ureide)-5-nitro-phenol were added to 600 ml of alcohol, and the solution was subjected to hydrogenation treatment by the addition of a palladium-carbon catalyst under normal pressure. After the consumption of hydrogen in the theoretical amount, the mixture was heated and the palladium-carbon catalyst was filtered off while in the heated condition. The filtrate was concentrated under reduced pressure, and to the produced residuum was added n-hexane to deposit crystals which were then collected by filtration and then washed, thereby containing 14 g of a white solid.

3.4 g of 5-amino-4-chloro-2-(2,4-dimethoxyphenyl ureide) phenol were added to 100 ml of an acetonitrile solution containing 0.9 ml of pyridine, and to the solution, with stirring at room temperature were added dropwise 50 ml of an acetonitrile solution consisting 5.5 g of 3-(m-hexadecyl sulfoneamide phenoxy)butyloyl chloride. After completion of the dropping, the reaction of the mixture took place for one hour, and then the mixture was poured into water. The resulting oily product was extracted by use of ethyl acetate. The thus produced oily substance was refined by use of silica gel and through column chromatography, and finally solidified using n-hexane, thus obtaining 3.7 g of a white solid. The structure of the product was ascertained through the procedures of nuclear magnetic resonance and mass spectrometry.

SYNTHESIS EXAMPLE 2

(Synthesis of Exemplified Coupler 19)

Synthesis of 4-chloro-5-(m-hexadecyloxycarbonyl benzoylamide)-2-(2,4-di-methoxyphenyl ureide)phenol.

3.4 g of 5-amino-4-chloro-2-(2,4-dimethoxyphenyl ureide) phenol were added to a mixture solution of 100 ml of acetonitrile and 0.9 ml of pyridine, and to the solution, with stirring at room temperature, were little by little added 4.5 g of m-hexadecyl-oxycarbonyl-benzoyl chloride. After completion of the addition, the reaction took place for one hour, and then the reaction product was poured into water. The resulting oily product was extracted by use of ethyl acetate, was subjected to silica gel-column chromatography to be refined, and was then solidified by use of n-hexane, whereby 2.7 of a white solid were obtained. The structure of the thus obtained product was ascertained through the procedures of nuclear magnetic resonance and mass spectrometry.

To the cyan dye forming coupler of the present invention, ordinary methods and techniques intended to be used for ordinary cyan dye forming couplers may be applied. In a typical manner, the coupler is incorporated into a silver halide emulsion, and this emulsion is coated on a base to thereby form a photographic element.

The photographic element may be either a monochromatic or a multicolor element. In the case of a multicolor element, the cyan dye forming coupler is normally incorporated into a red-sensitive emulsion. However, an unsensitized emulsion or each component unit provided with a dye image forming component unit having its sensitivity in the relevant one of three primary color regions of the spectra may be composed of either a single emulsion layer or a multi-coated emulsion layers. The layers of the element, including each image forming component unit may be arranged in various orders as is well-known to those skilled in the art. A typical multicolor photographic element comprises a base provided thereon with a cyan dye image forming component unit composed of at least one red-sensitive silver halide emulsion layer containing at least one cyan dye forming coupler (at least one of the cyan dye forming couplers is the coupler of the present invention), a magenta dye image forming component unit composed of at least one green-sensitive silver halide emulsion layer containing at least one magenta dye forming coupler, and a yellow dye image forming component unit composed of at least one blue-sensitive silver halide emulsion layer containing at least one yellow dye forming coupler. The element may be provided with additional layers such as filter layers, interlayers, a protective layer, a subbing layer, and the like.

The incorporation of the coupler of the present invention into an emulsion layer may be performed in conventionally known manners. For example, a single coupler or couplers in combination in the present invention are dissolved into such a high boiling organic solvent whose boiling point is not less than 175° C. as tricresyl phosphate, dibutyl phthalate, or the like or such a low boiling solvent as butyl acetate or butyl propionate or, if necessary, a mixture of some of these solvents, and the solution obtained is subsequently mixed with an aqueous gelatin solution containing a surfactant. The resulting mixture is emulsified by means of a high-speed rotary mixer or a colloid mill, and then added to a silver halide to thereby prepare a silver halide emulsion intended for use in the present invention. And the adding amount of the coupler of the present invention to the silver halide emulsion of the present invention is normally within the range of from about 0.07 to 0.7 mol, and preferably from 0.1 to 0.4 mol per mol of the silver halide.

Silver halides applicable to the silver halide emulsion of the present invention are those used in ordinary silver halide emulsions and include silver bromide, silver chloride, silver iodobromide, silver chlorobromide, silver chloroiodobromide, and the like.

Silver halide emulsions that may constitute the silver halide emulsion of the present invention may be prepared by various methods such as, in addition to ordinary methods, the method for the preparation of the so-called conversion type emulsion, as described in Japanese Patent Examined Publication No. 7771/1971, which is such that an emulsion of silver halide particles at least a part of which has a larger solubility than that of silver bromide is formed, and at least a part of the particles is then converted into silver bromide or silver iodobromide; the method for the preparation of Lippman type emulsion comprised of a fine-grained silver halide having a mean particle diameter of not more than 0.1μ; or other equivalent methods.

The silver halide emulsion of the present invention may be chemically sensitized by using singly or in combination a sulfur sensitizer such as aryl-thiocarbamide, thiourea, cystine, or the like; an active or inert selenium sensitizer; a reduction sensitizer such as a stannous salt, a polyamine, or the like, a noble metal sensitizer such as a gold sensitizer examples of which include potassium aurothiocyanate, potassium chloroaurate, 2-aurosulfobenzothiazol-methyl chloride, and the like; or a water-soluble salt sensitizer such as of ruthenium, rhodium, iridium, or the like, examples of which include ammonium chloropalladate, potassium chloroplatinate, sodium chloroapalladite, or the like.

The silver halide emulsion of the present invention may contain various known photographic additives such as those described in Research Disclosure Item No. 17643 (December 1978)

In order to render the silver halide of the present invention sensitive to the necessary wavelength region to which any red-sensitive emulsion is to be sensitive, the silver halide is spectrally sensitized by an appropriately selected sensitizer. For the spectral sensitization, there may be used singly or in combination various spectral sensitizers typical examples of which include cyanine dyes, merocyanine dyes, combined cyanine dyes, as described in, e.g., U.S. Pat. Nos. 2,269,234, 2,270,378, 2,442,710, 2,454,630, 2,776,280, and the like.

A color developing bath intended for use in the present invention is one that contains as the principal component thereof an aromatic primary amine color developing agent examples of which include p-phenylenediamines such as, e.g., diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, 2-amino-5-(N-ethyl-N-β-methanesulfoneamide ethyl)aminotoluene sulfate, 4-(N-ethyl-N-β-methanesulfoneamide ethylamino)aniline, 4-(N-ethyl-N-β-hydroxyethylamino) aniline, 2-amino-5-(N-ethyl-N-β-methoxyethyl)aminotoluene, and the like.

The development is followed by such normal processes as bleaching, fixing or bleach-fixing for the removal of the silver and silver halide, washing and then drying.

The present invention is illustrated in further detail with reference to examples, but the embodiment of the present invention is not limited thereto.

EXAMPLE 1

0.03 mole of each of the couplers of the present invention as shown in Table 1 and couplers (A), (B) and (C) given below was added to a liquid prepared by mixing dibutyl phthalate in the same amount by weight as that of each of the above couplers with ethyl acetate in the amount three times that of the dibutyl phthalate, and the coupler was completely dissolved by stirring with heating to 60° C. The resulting solution was added to an aqueous gelatin solution containing Alkanol B (alkyl-naphthalene sulfonate, manufactured by DuPont) and emulsified by means of a colloid mill to thereby prepare coupler-dispersed liquids, respectively. Each of the resulting coupler-dispersed liquids was added to a silver chlorobromide emulsion containing 0.1 mole of silver, and the thus produced emulsions each was coated on a polyethylene-laminated paper and then dried, whereby six different stable layer-having silver halide color photographic light-sensitive materials were obtained (Sample Nos. (1) to (6)).

Control Coupler (A)

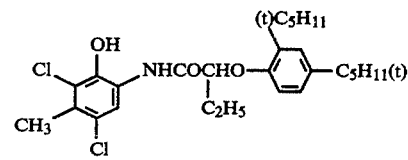

Control Coupler (B)

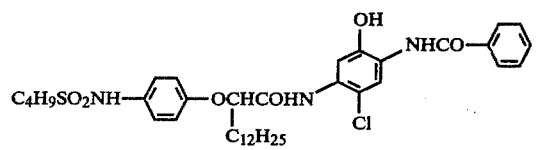

Control Coupler (C)

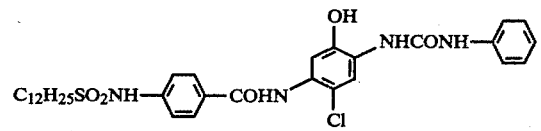

These samples were exposed through an optical wedge to light in the normal sensitometric procedure, and then processed in the following steps, provided the color developing in the steps was carried out in two different composition baths: one to which was added benzyl alcohol (color developing bath composition (1)

and the other without benzyl alcohol (color developing bath composition (2).

| Processing steps (at 30° C.) | Processing period |
|---|---|
| Processing steps: | |
| Color developing | 3 min. 30 sec. |
| Bleach-fixing | 1 min. 30 sec. |
| Washing | 2 min. |

The respective bath compositions are as follows:

Color developing bath composition 1:
| | |
|---|---|
| 4-amino-3-methyl-N—ethyl-N— (β-methane-sulfoneamide ethyl)- aniline sulfate | 5.0 g |
| Benzyl alcohol | 15.0 ml |
| Sodium hexametaphosphate | 2.5 g |
| Anhydrous sodium sulfite | 1.85 g |
| Sodium bromide | 1.4 g |
| Potassium bromide | 0.5 g |
| Borax | 39.1 g |
| Water to make 1 liter. Add sodium hydroxide to adjust the pH to 10.30. | |

Color developing bath composition 2:
| | |
|---|---|
| 4-amino-3-methyl-N—ethyl-N— (βmethane-sulfoneamide ethyl)- aniline sulfate | 5.0 g |
| Sodium hexametaphosphate | 2.5 g |
| Anhydrous sodium sulfite | 1.85 g |
| Sodium bromide | 1.4 g |
| Potassium bromide | 0.5 g |
| Borax | 39.1 g |
| Water to make 1 liter. Add sodium hydroxide to adjust the pH to 10.30. | |

Bleach-fixing bath composition:
| | |
|---|---|
| Iron-ammonium ethylenediamine tetraacetate | 50 g |
| Ammonium sulfite (40% aqueous solution) | 50 ml |
| Ammonium thiosulfate (70% aqueous solution) | 140 ml |
| Aqueous ammonia (28% solution) | 20 ml |
| Ethylenediamine tetraacetate | 4 g |
| Water to make 1 liter | |

The respective samples thus processed were measured for their photographic characteristics. The results are as shown in Table 1. The relative photographic speeds shown in Table 1 are those relative to the maximum speed regarded as 100 of the sample containing Control coupler (A) processed in the color developing bath composition 1.

TABLE 1

| Sample No. | Coupler used | Color developing bath composition 1 | | Color developing bath composition 2 | |
|---|---|---|---|---|---|
| | | Relative speed | Maximum density | Relative speed | Maximum density |
| 1 | Exemplified compound - 4 | 110 | 2.30 | 95 | 2.00 |
| 2 | Exemplified compound - 14 | 105 | 2.24 | 70 | 1.85 |
| 3 | Exemplified compound - 20 | 100 | 2.20 | 85 | 1.90 |
| 4 | Control coupler - A | 100 | 2.20 | 50 | 1.40 |
| 5 | Control coupler - B | 95 | 1.95 | 61 | 1.50 |
| 6 | Control coupler - C | 90 | 1.80 | 55 | 1.51 |

As apparent from Table 1, the samples obtained by use of the couplers of the present invention, regardless of whether benzyl alcohol is used or not, are found out to be excellent in their speeds and maximum densities.

As the result of measuring the spectra of the color developed, the dyes formed from the couplers of the present invention were found out to be excellent in the color purity having absorption wavelength maximums in the relatively longer wavelength portion and little absorption in the shorter wavelength portion in the red region of the spectra.

EXAMPLE 2

Samples obtained in the same manner as in Example 1 were used to examine the light resistance, heat resistance and moisture resistance thereof. The results of these tests are as shown in Table 2.

TABLE 2

| Sample No. | Coupler used | Color developing bath composition 1 | | | Color developing bath composition 2 | | |
|---|---|---|---|---|---|---|---|
| | | Light resistance | Heat resistance | Moisture resistance | Light resistance | Heat resistance | Moisture resistance |
| 7 | Exemplified compound - 4 | 90 | 100 | 96 | 90 | 98 | 95 |
| 8 | Exemplified compound - 14 | 85 | 100 | 95 | 85 | 97 | 93 |
| 9 | Exemplified compound - 20 | 85 | 100 | 93 | 85 | 97 | 93 |
| 10 | Control coupler - A | 90 | 45 | 60 | 85 | 47 | 63 |
| 11 | Control coupler - B | 60 | 90 | 92 | 60 | 95 | 90 |
| 12 | Control coupler - C | 55 | 90 | 92 | 55 | 95 | 90 |

In addition, the values given in the light resistance columns of the table are the relative values of the residual density obtained after exposing the respective resulting images to the light of a xenon fadometer for the duration of 300 hours to the corresponding sensitivity values regarded as 100 of the same samples prior to exposing to the light. The values in the moisture resistance columns of the table are the relative residual density values after aging the samples under the condition of 60° C./70% RH for the duration of three weeks to the corresponding density values regarded as 100 of the samples before the aging. And for the heat resistance, the residual densities of the samples after being subjected to aging under the condition of 77° C. over a period of three weeks are given in the relative values to the corresponding values regarded as 100 of the samples before the aging (provided the initial density is 1.0).

As apparent from Table 2, Control Coupler (A) shows an excellent resistance against light, but has a drawback in the heat resistance, while Control Couplers (B) and (C) are excellent in the heat resistance, but have a problem in the light resistance.

While on the other hand, Exemplified Couplers (4), (14) and (20) are found out to have excellent characteristics in every aspect.

EXAMPLE 3

0.01 mole of each of the couplers of the present invention as given in Table 3, Control Couplers (A) and (B) and Control Coupler (D) having the formula given below was taken to be added to a mixture liquid of tricresyl phosphate in the same amount by weight as that of each of the above couplers and ethyl acetate in the amount three times that of the tricresyl phosphate, and the coupler was completely dissolved by stirring with heating to 60° C. This solution was added to an aqueous gelatin solution containing Alkanol B and emulsified by means of a colloid mill to thereby prepare each coupler-dispersed liquid.

The coupler-dispersed liquid is subsequently added to an iodobromide (6 mole% silver iodide) emulsion containing 0.1 mole of silver, and the resulting emulsion was coated on a cellulose acetate film base and then dried, thus obtaining six different, stable layer-having silver halide color photographic light-sensitive materials (sample Nos. (13)–(18)).

Control Coupler (D)

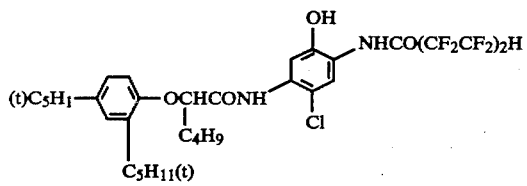

Each of these samples was exposed through an optical wedge to light in accordance with the normal sensitometric procedure and then subjected to processing in the following steps:

Processing steps:

| Processing steps (at 33° C.) | Processing period |
| --- | --- |
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |

Color developing bath composition:

| | |
| --- | --- |
| 4-amino-3-methyl-N—ethyl-N— (β-hydroxyethyl)-aniline sulfate | 4.8 g |
| Anhydrous sodium sulfite | 0.14 g |
| Hydroxyamine, ½ sulfate | 1.98 g |
| sulfuric acid | 0.74 g |
| Anhydrous potassium carbonate | 28.85 g |
| Anhydrous potassium hydrogencarbonate | 3.46 g |
| Anhydrous potassium sulfite | 5.10 g |
| Potassium bromide | 1.16 g |
| Sodium chloride | 0.14 g |
| Trisodium nitriloacetate | 1.20 g |
| Potassium hydroxide | 1.48 g |
| Water to make 1 liter | |

Bleaching bath composition:

| | |
| --- | --- |
| Iron-ammonium ethylenediamine tetraacetate | 100 g |
| Diammonium ethylenediamine tetraacetate | 10 g |
| Ammonium bromide | 150 g |
| Glacial acetic acid | 10 ml |
| Water to make 1 liter. Add aqueous ammonia to adjust the pH to 6.0 | |

Fixing bath composition:

| | |
| --- | --- |
| Ammonium thiosulfate | 75.0 g |
| Anhydrous sodium sulfite | 8.6 g |
| Sodium metasulfite | 2.3 g |
| Add water to make 1 liter. Add acetic acid to adjust the pH to 6.0 | |

Stabilizing bath composition:

| | |
| --- | --- |
| Formalin (37% aqueous solution) | 1.5 ml |
| Koniducks (manufactured by Konishiroku Photo Industry Co., Ltd.) | 7.5 ml |
| Water to make 1 liter | |

The thus cyan color-developed image was measured for the photographic characteristics thereof. The results are as shown in Table 3.

TABLE 3

| Sample No. | Coupler used | Relative speed | Maximum density |
| --- | --- | --- | --- |
| 13 | Exemplified compound - 5 | 120 | 2.00 |
| 14 | Exemplified compound - 8 | 100 | 1.70 |
| 15 | Exemplified compound - 19 | 110 | 1.90 |
| 16 | Control coupler - A | 100 | 1.70 |
| 17 | Control coupler - B | 95 | 1.65 |
| 18 | Control coupler - D | 80 | 1.50 |

As apparent from Table 3, the samples in which the couplers of the present invention were used are excellent in the photographic speed as well as in the color developability.

Each of the samples of the present invention, as the result of measuring the absorption spectrum thereof, was found out to have the absorption maximum in the longer wavelength portion and shows a sharp-cut end in the shorter wavelength portion in the red region to provide a desirable dye image for the color reproduction in the green region as compared to the control couplers.

EXAMPLE 4

Each of Samples (1) to (6) obtained in Example 1, after being exposed through an optical wedge to light, was processed in the bath of color developing bath composition 1 in Example 1, and then a part of each of the developed samples was processed in the foregoing bleach-fixing bath while the other part was processed in an exhausted bath-simulated bleach-fixing solution of the following composition to thereby examine possible discolorations of the formed cyan dyes due to the exhaustion of a bleach-fixing bath.

Bleach-fixing bath composition:

| | |
| --- | --- |
| Iron-ammonium ethylenediamine tetraacetate | 50 g |
| Ammonium sulfite (40% aqueous solution) | 50 ml |
| Ammonium thiosulfate (70% aqueous solution) | 140 ml |
| Aqueous ammonia (28% solution) | 20 ml |
| Ethylenediamine tetraacetate | 4 g |
| Sodium hydrosulfite | 5 g |
| Water to make 1 liter | |

Each of the thus processed samples was measured for the maximum reflection density of the formed cyan dye thereof. The results are as shown in Table 4.

In addition, the residual rate of the dye in the maximum density area was determined by the following formula:

$$\text{Residual rate of dye} = \frac{\text{Exhausted bleach-fixing bath processing}}{\text{Fresh bleach-fixing bath processing}} \times 100$$

TABLE 4

| Coupler used | Fresh BF* processing | Exhausted BF* processing | Residual rate of dye |
| --- | --- | --- | --- |
| Exemplified compound - 4 | 2.30 | 2.25 | 98 |
| Exemplified compound - 13 | 1.90 | 1.90 | 100 |
| Exemplified compound - 20 | 2.20 | 2.10 | 95 |
| Control coupler - A | 2.20 | 1.43 | 65 |
| Control coupler - B | 1.95 | 1.93 | 99 |
| Control coupler - C | 1.80 | 1.72 | 96 |

Note:
*"BF" stands for Bleach-Fixing bath.

From Table 4 it is understood that the samples containing the couplers of the present invention show little discoloration of the formed cyan dyes in the exhausted bleach-fixing bath as compared to those containing the control couplers.

What is claimed is:

1. A method for forming a silver halide color photographic image comprising the step of forming a dye image in the presence of a phenol cyan coupler, said phenol cyan coupler having the formula:

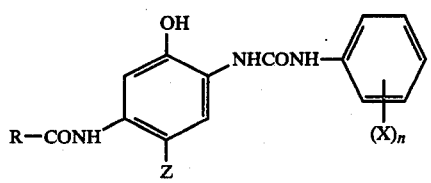

Formula (I)

wherein R is an alkyl, an aryl or a heterocyclic group; X is selected from the group consisting of an alkyl, acyloxy, acylamino, succinimide, piprolidine, piperidine and sulfoneamide moiety; Z is a hydrogen atom or a group capable of eliminating itself from said coupler during the coupling reaction thereof with the oxidized product of a color developing agent; and n is an integer from 1 to 3, wherein when n is 2 or 3, X may be the same or different.

2. A method according to claim 1, wherein the group capable of eliminating itself represented by Z is one selected from the group consisting of a halogen atom, an aryloxy group in which an oxygen atom or a nitrogen atom is directly attached to the coupling position thereof, a carbamoyloxy group, a carbamoylmethoxy group, an acyloxy group, a sulfoneamide group and a succinic acid imide group.

3. A method according to claim 1, wherein the alkyl group represented by R is a phenoxyalkyl group.

4. A method according to claim 1, wherein the acylamino group represented by X is alkyl carbamide group or a benzoylamide group.

5. A method according to claim 1, wherein the sulfoneamide group represented by X is an alkyl sulfoneamide group or a benzene sulfoneamide group.

6. A light sensitive silver halide photographic material comprising a support and a layer, said layer comprising a phenol cyan coupler having the formula

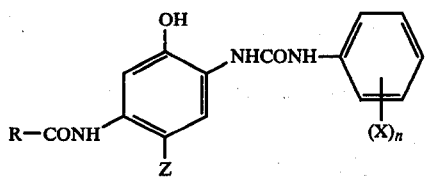

wherein R is an alkyl, an aryl or a heterocyclic group; X is selected from the group consisting of an alkyl, acyloxy, acylamino, succinimide and sulfoneamide moiety; Z is a hydrogen atom or a group capable of eliminating itself from said coupler during the coupling reaction thereof with the oxidized product of a color developing agent; and n is an integer from 1 to 3, wherein when n is 2 or 3, X is the same or different.

* * * * *